(12) United States Patent
Casagrande et al.

(10) Patent No.: US 7,987,717 B2
(45) Date of Patent: Aug. 2, 2011

(54) METHOD FOR NONCONTACT TESTING OF THE DEGREE OF HARDENING OF INK AND COATING FILMS

(75) Inventors: Magdalena-Elena Casagrande, Munich (DE); Thomas Walther, Offenbach (DE)

(73) Assignee: manroland AG, Offenbach (DE)

( * ) Notice: Subject to any disclaimer, the term of this patent is extended or adjusted under 35 U.S.C. 154(b) by 488 days.

(21) Appl. No.: 12/058,203

(22) Filed: Mar. 28, 2008

(65) Prior Publication Data

US 2008/0240763 A1   Oct. 2, 2008

(30) Foreign Application Priority Data

Mar. 28, 2007  (DE) .......................... 10 2007 015 366

(51) Int. Cl.
- *G01M 7/00* (2006.01)
- *G01B 21/08* (2006.01)
- *G01N 11/10* (2006.01)

(52) U.S. Cl. .................. 73/573; 73/150 R; 73/54.41

(58) Field of Classification Search ............... 73/150 R, 73/573, 574, 54.41
See application file for complete search history.

(56) References Cited

U.S. PATENT DOCUMENTS

| | | | | |
|---|---|---|---|---|
| 4,614,115 A | * | 9/1986 | Pelletier et al. ................. | 73/599 |
| 5,025,665 A | | 6/1991 | Keyes, IV et al. | |
| 5,693,375 A | * | 12/1997 | Sato et al. ..................... | 427/522 |
| 5,937,761 A | * | 8/1999 | Buschmann et al. ......  | 101/424.1 |
| 6,481,289 B2 | * | 11/2002 | Dixon et al. .................... | 73/602 |
| 2008/0240762 A1 | * | 10/2008 | Casagrande ................... | 399/67 |

FOREIGN PATENT DOCUMENTS

| | | |
|---|---|---|
| DE | 24 58 935 A1 | 4/1977 |
| DE | 27 25 093 A1 | 12/1978 |
| DE | 30 45 581 A1 | 9/1981 |
| DE | 43 18 445 B4 | 12/1994 |
| DE | 197 37 785 A1 | 3/1999 |
| DE | 100 04 212 C1 | 7/2001 |
| DE | 103 181 04 A1 | 11/2004 |
| DE | 10 2005 009 262 A1 | 8/2006 |
| EP | 1 142 711 B1 | 10/2001 |

* cited by examiner

*Primary Examiner* — Hezron Williams
*Assistant Examiner* — Nathaniel Kolb
(74) *Attorney, Agent, or Firm* — Leydig, Voit & Mayer, Ltd.

(57) ABSTRACT

For more efficient and energy-saving drying of ink and/or coating films in printing machines, the drying or hardening process must be better monitored. Therefore a method is proposed for determining the degree of hardening of one or more printed ink and/or coating films on a substrate that was coated in an intaglio, flexographic or offset printing process. The degree of hardening or drying due to the hardening or drying process is determined indirectly via the change of mechanical and/or viscoelastic properties of the ink and/or coating films on the substrate. An ultrasound measurement is used for this purpose.

26 Claims, No Drawings

METHOD FOR NONCONTACT TESTING OF THE DEGREE OF HARDENING OF INK AND COATING FILMS

This application claims priority to German Application No. 102007015366.1 filed Mar. 28, 2007, which herein is incorporated by reference in their entireties for all that they teach without exclusion of any portion thereof.

FIELD OF THE INVENTION

The present invention relates generally to a method for testing by means of ultrasound the degree of hardening of ink or coating films used in one of the mass production printing methods comprising offset, flexographic or intaglio printing.

BACKGROUND OF THE INVENTION

Ink and coating films must be hardened with one of the following processes: evaporation of solvents, absorption of solvents in the substrate, oxidation, by polymerization with the aid of UV or electron beam dryers, or by combinations of the above-mentioned drying mechanisms.

Monitoring the hardening of ink and coating films appears reasonable due to a number of factors. A sufficient drying and hardening of the printed inks or coatings is a prerequisite for high-quality printing. In the area of the conveyance path of sheets through a machine, contact of the freshly printed or coated sheet surface with sheet guiding elements can lead to damage, which results in print spoilage (rejects) in the printed product. The printed products stored in the delivery unit of a sheet-fed printing machine, or in the web reels of a web-fed printing machine, must be sufficiently dry with respect to the printed inks or coatings, since otherwise they would become smudged and stuck together during stacking or winding. The latter in particular would hinder further processing of the printed products or render it impossible.

Strict requirements must be placed on the adjustment of differently constructed dryer units. Already when the printing machine is being set up, the user must make adjustments to the dryer units in order to be able to produce the necessary quality after as short a time as possible and with as small a number of wasted sheets (feeding waste) as possible. An excessively high setting of the dryer power not only causes high power consumption of the printing machine and likewise a large waste heat power, which would raise the temperature of the printing room or have to be eliminated by the air-conditioning unit of the printing room, but also negatively affects the printing process itself. It is known that the tack and viscosity of ink/coating vary, so that under certain circumstances a high heating of the machine as well as the heating of the ink and the metering device could again cause waste. Adjustment parameters for the dryer action or dryer power that are selected too low must likewise be avoided, since otherwise the above-described danger of smudging of freshly printed sheets during sheet transport or in the delivery device exists.

By controlling the dryer, it is possible not only to reduce print spoilage, but also to save considerable energy. Since the dryer devices are only operated at the power that is necessary according to the current situation, the power consumption of the equipment is reduced to the respectively required value. Reduced heating of machine elements or the entire machine results, because the dryer devices also reduce waste heat. The service life of the machine or of machine components is thereby increased. Finally, a reduced dryer power also avoids raising the printing room temperature. Even for an air-conditioned room, this provides energy savings since less wasted heat is produced by the dryer.

Special issues arise for the printing of radiation-hardening inks and coatings since they require monitoring of the hardening in the printing machines. Printing with radiation-hardening offset ink has become widely disseminated in the printing industry. The advantages of printing with radiation-hardening inks lie in the rapid spontaneous polymerization after irradiation with a UV radiation source, the lack of solvents in the ink, and the good printability on non-absorptive substrates (films).

Conventional inks, on the other hand, are either oil-based or contain solvents. Oil-based inks dry by oxidation of the oil-based binders, or they dry by evaporation of the easily volatilized oils in the ink (heat set method). In contrast, radiation-hardening inks and coatings are hardened by a photo-chemical process, also referred to as polymerization. The liquid or unpolymerized ink film is transformed into a solid state by polymerization under the influence of UV light.

Malfunctions are known in which unpolymerized ink components are transferred to the back of the substrate above them by blotting in the delivery stack of a sheet-fed printing machine or by blotting in a reel after printing. Ink components can also migrate through the substrate. For packaging, migration of ink components or blotting of ink can lead to a sensory effect on the packaged material. If specific migration limits are exceeded in food packaging, harm to the health of consumers cannot be ruled out. If the specific migration limits are exceeded, packages must be withdrawn from the market, which, in addition to the financial consequences, results in lost reputation of the brand's manufacturer. Maintenance of harmlessness to health is paramount. According to §30 LMBG [Food Safety Act], it is prohibited to manufacturer consumer articles in such a manner that, when used as directed, they are liable to be harmful to health due to their material composition, in particular, due to toxicologically active substances or contamination. Moreover, according to German and European law, and in the USA as well, the "no migration principle" applies, i.e., transfer of substances to the packaged foodstuffs must be avoided. Therefore, it is particularly important to ensure the polymerization of the radiation-hardening ink on the substrate in all cases.

Incompletely hardened radiation-hardening inks and coatings also have effects on the safety of the operating personnel. For example, if such ink or coating films on the substrate are incompletely hardened and a machine operator takes samples to check the print quality, migration-capable components of radiation-hardening ink may be absorbed through the skin. In addition to health risks, irritation and allergic skin reactions can occur. The printing plant also incurs additional disposal costs from incompletely hardened inks and coatings, since printed sheets with unpolymerized ink or coating components must generally be treated as hazardous waste. This requires extra logistical effort and generally produces excess costs for disposal.

Many factors therefore suggest that the hardening or drying of ink and coating films on the substrate should be measured, measurement parameters formed, and they should be used to control the dryer directly or via user input. Additionally, quality protocols can be formed from these measured values, which will give the end-user verification that the ink or coating has been sufficiently hardened. This is often demanded specifically in the field of radiation-hardening inks and coatings.

The desire to evaluate the hardening or drying of ink and coating films has already been widely discussed. In EP 1 142

711 B1 it is proposed that a controller for the dryer device be provided, to which at least one signal of a parameter characterizing the printing process is supplied, and that, consequently, signals be generated by the controller with which the operating mode of the dryer device is modified in a predetermined manner. It is also proposed to undertake the controlling of the dryer unit on the basis of values measured on the substrate. The coating or ink film thickness or the gloss of the coating deposition are mentioned as measurement parameters.

DE 197 37 785 A1 proposes to determine the degree of drying of a coating film by measuring the intensity of a microwave signal that interacts with the coated substrate. The state parameter formed from the measurement signal can then be utilized as a control parameter for controlling the dryer. However, the method is suitable only for use of coating media that absorb microwave energy to a large extent, such as dispersion varnish, which has essentially only water as a solvent. Testing the polymerization of hardened ink and coating films was not mentioned in the patent.

DE 24 58 935 A1 discloses a method for measuring and controlling the speed of printing and coating machines, in which the wavelengths corresponding to the solvents that are used are continuously analyzed on the paper webs, with the average values measured after drying being compared to the preset maximum values. The measurement unit contains an analyzer head with continuous emission of radiation and a receiver for receiving the radiation that the product to be analyzed reflects or that passes through the latter. The disadvantage of this method is that the solvent composition must be known in advance. This is relatively simple for printing processes that operate with simple solvent compositions, but the complexity increases for modern ink with a number of solvents. The supplier generally discloses the composition of the ink only in approximate amounts of the constituents. This method also fails for printing processes that do not emit any solvent. These include, among others, radiation-hardening printing processes, as well as oxidative and ink absorption processes. This measurement method is not universally applicable. Moreover, using it for fast-running printing machines is known, since the analysis is time-intensive and complex.

Optical or Raman spectroscopy are used in the laboratory for assessing polymerization. Due to their complexity and the required preparation of specimens, these methods are not well suited for use in the rough machine environment of a printing plant. Determining the degree of polymerization from the change of physical/mechanical properties of the ink or coating film has accordingly been considered. One possibility is the determination of the coefficient of sliding friction of the surface, which changes with increasing degree of polymerization. The disadvantage of this method is that it can only act on the surface, and the depth-hardening can only be determined approximately. Moreover, the measurement of sliding friction is a contact method, which can lead to damage on the surface of the ink or coating.

Ultrasound measurements are known as a measuring method in the printing industry. Test methods with ultrasound have the advantage that they are noninvasive and nondestructive techniques for determining the properties of a material.

One known approach for checking the strength of paper webs is the measurement of the propagation velocity and intensity of acoustic waves in these webs. Such a method and a device for nondestructive examination of paper in a continuous, rapidly moving web during manufacturing are described in DE 30 45 581 A1. This method exploits the fact that many strength parameters of paper are related to a modulus of elasticity. The latter can be correlated with the velocity of acoustic waves propagating through the paper web. A transmitting acoustic source or transducer transmits a mechanical signal to the paper, and a receiver receives the ultrasound signal from the paper. With knowledge of the time that ultrasonic signals require for propagation through the paper and of the distance that these acoustic waves travel, the velocity of the acoustic waves can be calculated. The transducers are arranged according to this invention on wheels that are in physical contact with the paper web. Because of this contact and the strict requirements for synchronization of the wheels, the invention is not very practical. Such a measurement on printed paper webs appears to be very difficult due to the contact.

A measurement in which there is a non-contacting coupling of acoustic waves would therefore be desirable. As a non-contacting measurement of the flexibility of banknotes, DE 103 18 104 A1 proposes irradiating them with acoustic waves, detecting the acoustic waves coming from the sheet material, measuring the transmitted and reflected acoustic waves, and deriving values for the flexibility of the sheet material therefrom that are independent of the degree of soiling of the banknote. The disadvantage of the solution that was found is, among other things, that the acoustic receivers are arranged on both sides of the paper. Moreover, only transmitted or reflected acoustic waves are evaluated; the propagation of the acoustic waves on the surface is not taken into account.

Ultrasound is also used in industry for measuring the thickness of ink films on rollers and the substrate. DE 43 18 445 B4 describes a method that determines the film thickness of an ink by differential transit times.

The problem of the invention is therefore to determine the hardening or drying of coating or ink films applied to paper, film or cardboard substrates in a printing process.

This problem is solved by the characteristics of claim 1.

OBJECTS AND SUMMARY OF THE INVENTION

For more efficient and energy-saving drying of ink and/or coating films in printing machines, the invention provides an improved system for monitoring the drying or hardening process. In particular, an improved method is proposed for determining the degree of hardening of one or more printed ink and/or coating films on a substrate that was coated in an intaglio, flexographic or offset printing process. The degree of hardening or drying due to the hardening or drying process is determined indirectly via the change of mechanical and/or viscoelastic properties of the ink and/or coating films on the substrate. An ultrasound measurement may be used for this purpose.

In an embodiment of the invention, the wavelength of the laser is selectable and tunable to the absorption characteristic of the ink and/or coating film. In another embodiment of the invention, a nominal signal for analysis is derived from a mathematical model. A characteristic value of the state of the ink and/or coating film obtained by the signal analysis is a percentage indication of the degree of hardening or drying in another embodiment of the invention. It will be appreciated that in a further embodiment of the invention, the measuring units are connected to the machine via a data line or wireless data link.

Other objects and advantages of the invention will become apparent upon reading the following detailed description.

While the invention is susceptible of various modifications and alternative constructions, a certain illustrative embodiment thereof will be described below in detail. It should be understood, however, that there is no intention to limit the invention to the specific form disclosed, but on the contrary, the intention is to cover all modifications, alternative constructions, and equivalents falling within the spirit and scope of the invention.

DESCRIPTION OF THE PREFERRED EMBODIMENTS

Ultrasound can be introduced into the material by transducers, for example, piezoelectric or magnetoresistive transducers. Ultrasound can also be generated in the material by a laser pulse or a plasma, however. Sound waves induced by lasers have many advantages. They require no contact with the material to be tested, allow fast inspection and are nondestructive if the light energy is selected to be sufficiently low. Laser-induced ultrasound can be generated very well in industrial environments such as a printing machine. The ultrasound generation is then not dependent on contact between the material and the signal transmitter, as is the case with piezoelectric transducers, for example. The focus of the laser beams can be selected to be very small, so that targeted measurements at defined positions are possible. Laser-induced ultrasound waves also have disadvantages with respect to the conventional coupling via transducers, however, since they are more expensive and sometimes have a lower sensitivity.

The mechanisms of ultrasound generation in a solid can be described as follows. A pulsed laser beam is directed onto the material to be tested and partially absorbed by the latter. The light energy that is directed onto the material is converted into heat energy, whereby a very rapid local thermal expansion of the material takes place. This leads to the generation of ultrasound in the medium. If the light energy is selected to be sufficiently low, the material is not melted or ablated. If the light energy is high and the material melts and this leads to the generation of a plasma, ultrasound is again generated, but by a transfer of torque during the detachment of the material. This ablative process is not acceptable in the printed image, but can possibly be tolerated in marginal areas of the printed sheet, for example, in the area of the control strip, which is later discarded.

The hardening or drying of an ink or coating film can be assessed with ultrasound. The ink and/or the coating undergo a marked change of viscosity during hardening or drying. In the case of a radiation-hardening ink or coating film, it is available in hardened form immediately after irradiation with UV light or electron beams. There is a close relationship between the material properties and the acoustic parameters. When ultrasound waves are induced in an ink or coating film, longitudinal and transverse sound waves are influenced by the structure and by the molecular relaxation process. Ultrasound methods are therefore very well suited to determine mechanical moduli. In non-homogeneous ink and coating films, morphological information can be determined by sound scattering and reflection. The formation of ink and coating films can be observed by this method by way of the change in the mechanical properties of print and coating films. Echoes of the longitudinal and transverse sound waves are observed and analyzed in an analysis software. Familiar techniques such as Fourier transforms and time-slot techniques can be used in such a signal analysis.

Measurements of the mechanical moduli of ink and coating films generally take place at very high frequencies in the MHz to the GHz range. However, the mechanical properties in the low-frequency range can also be of interest. Pulses that do not contain only one frequency can also be generated. By using a broad, continuous frequency spectrum, the hardening state can be precisely defined, because different frequency components are differently transmitted depending on the hardening state. After the measurement, the spectrum can be analyzed using a Fourier transform. From this, frequency-time curves or frequency-time surfaces can be derived, which present an interpretation of the spectral properties of an ink or coating film as a function of time.

It is possible to improve the measurement by placing the specimen on a material such as glass or quartz that reflects ultrasound very well. The ultrasound reflected from this material has a smaller amplitude and is phase-shifted after reflection. The attenuation and the phase shift are characteristic markers of a material.

It is also known that the viscoelastic behavior of materials changes with the frequency of the ultrasound and also with the temperature of the specimen. These two parameters of influence must be taken into consideration in the interpretation of the data.

Ultrasound echoes can be detected with transducers or optical measuring devices such as interferometers. The data obtained from the measurement regarding the mechanical moduli of the ink and coating films can be evaluated and assessed as absolute measured values, in comparison with reference values stored in an expert system or a data storage unit, or in comparison to a specimen with defined hardening properties. The hardening or drying of ink and coating films is preferably summarized in a characteristic number that makes it possible to intervene for control purposes without a great deal of interpretation of curve profiles by adapting machine parameters such as dryer temperature, radiation power machine speed and so on to the requirements.

The adjustment can take place automatically if the results of the hardening and drying measurement are directly taken over from the machine controller and the appropriate measures are defined from them. In the simplest case, the machine operator receives suggested settings. In more complex cases, corrective measures are initiated via characteristic curves, calculation rules or other knowledge stored in an expert system. On the one hand, this could improve drying in case of an insufficient hardening or drying. If drying is sufficient, on the other hand, the controller can also be used to reduce the dryer power to save energy.

The approach of determining the degree of hardening or drying by measuring the mechanical characteristic parameters allows a monitoring of the hardening that can even be used in the rough environment of a printing plant. It can be done offline outside the machine, or inline while the machine is running. With this approach, for the first time it is possible to obtain, with a tolerable amount of effort, a production protocol with statistics, curve profiles or characteristic numbers that makes it possible for the printer to verify sufficient drying or hardening, and thus reliable production, to the end user.

The invention claimed is:
1. A method for determining the degree of hardening of one or more printed ink or coating films on a substrate selected from the group consisting of paper, cardboard, plastic film or composite materials, in an offset printing process, the method comprising:
measuring a change of one of the mechanical and viscoelastic properties of the ink or coating films on the substrate by externally causing an ultrasonic oscillation or an ultrasound signal in the ink or coating film and analyzing the echo from the ultrasonic oscillation or ultrasound signal to determine mechanical or viscoelas- tic properties of the ink or coating film while the substrate is passing through a printing press used for the printing process; and determining the degree of hardening or drying of the printed ink or coating films via the measured change of mechanical or viscoelastic properties, wherein the ultrasound signal is externally caused by one of a laser beam and a laser pulse directed to the ink or coating film, wherein a rapid local expansion of the ink or coating film takes place due to the thermal energy of the laser beam or pulse, leading to the generation of ultrasound in the ink or coating film.

2. The method according to claim 1, wherein the ultrasound signal is externally caused by one of an ultrasound signal or laser pulse introduced into the ink or coating film and wherein the ultrasound signal or laser pulse introduced into the ink or coating film or the ultrasound signal generated in the ink or coating film is frequency-modulated.

3. The method according to claim 2, wherein pulses having only one frequency or wavelength are emitted by an ultrasound transducer or the laser source.

4. The method according to claim 2, wherein the pulses emitted by an ultrasound transducer or the laser source sweep continuously or discretely through a frequency or wavelength spectrum.

5. The method according to claim 1, wherein the ultrasound signal is externally caused by one of an ultrasound signal or a laser pulse introduced into the ink or coating film, and wherein the ultrasound signal or the laser pulse introduced into the ink or coating film or the ultrasound signal generated in the ink or coating film, is intensity-modulated and frequency-modulated.

6. The method according to claim 1, wherein the wavelength of the laser is selectable and tunable to the absorption characteristic of the ink or coating film.

7. The method according to claim 1, wherein echoes from sound waves in the transverse or longitudinal direction are detected by corresponding sensors.

8. The method according to claim 7, wherein the sensors are constructed as ultrasonic transducers.

9. The method according to claim 7, wherein the sensors are constructed as optical measuring devices for detecting the propagation of the sound waves in the ink or coating film.

10. The method according to claim 1, further comprising performing a signal analysis of the detected signals, wherein there is a communicative coupling with a sensor that detects the ultrasound signal, and wherein measurement signals are received from the sensor for signal analysis and these measurement signals are evaluated.

11. The method according to claim 10, wherein the signal analysis is performed by comparing the measured signal to a nominal signal.

12. The method according to claim 11, wherein the nominal signal is derived from a mathematical model.

13. The method according to claim 11, wherein the nominal signal is taken from the memory of an expert system.

14. The method according to claim 11, wherein the expected nominal signal is obtained from a reference measurement.

15. The method according to claim 10, wherein one or more characteristic values for characterizing the physical state of the dried ink or coating film are formed by means of the signal analysis.

16. The method according to claim 15, wherein a characteristic value of the state of the ink or coating film obtained by the signal analysis is a percentage indication of the degree of hardening or drying.

17. The method according to claim 10, wherein the results of the signal analysis are displayed on a display device, and in that the display are combined with suggested actions for adjusting the dryer device or the machine parameters.

18. The method according to claim 17, wherein the results are output at the management console of a printing machine.

19. The method according to claim 10, wherein control signals are automatically obtained for changing the setting of the process parameters influencing the drying or hardening, and these signals are transferred to one or more control units, the signal transfer taking place to accomplish a changing of the process parameters.

20. The method according to claim 1, wherein the measurement takes place offline, outside the machine, with a separate measuring device.

21. The method according to claim 1, wherein the measurement takes place inline, during a print run through the machine, by means of a measuring unit.

22. The method according to claim 1, wherein the measuring units are connected to the machine via a data line or wireless data link.

23. The method according to claim 1, wherein printed products that are produced in web-fed printing machines are measured.

24. The method according to claim 1, wherein the determination of the change of mechanical or viscoelastic properties of ink or coating films on the substrate is performed on radiation-hardening ink or coating films that were hardened with UV radiation or electron beam drying.

25. The method according to claim 1, wherein the determination of the change of mechanical or viscoelastic properties of ink or coating films on the substrate is performed on solvent-containing or water-containing inks.

26. The method according to claim 1, wherein the determination of the change of mechanical or viscoelastic properties of inks on the substrate is performed on inks that dry oxidatively or by absorption into the substrate.

* * * * *